(12) United States Patent
Bian

(10) Patent No.: US 8,338,577 B2
(45) Date of Patent: Dec. 25, 2012

(54) METHODS FOR QUANTIFYING PROTEIN LEAKAGE FROM PROTEIN BASED AFFINITY CHROMATOGRAPHY RESINS

(75) Inventor: Nanying Bian, Lexington, MA (US)

(73) Assignee: EMD Millipore Corporation, Billerica, MA (US)

( * ) Notice: Subject to any disclaimer, the term of this patent is extended or adjusted under 35 U.S.C. 154(b) by 651 days.

(21) Appl. No.: 12/584,931

(22) Filed: Sep. 15, 2009

(65) Prior Publication Data

US 2010/0112597 A1    May 6, 2010

Related U.S. Application Data

(60) Provisional application No. 61/192,082, filed on Sep. 15, 2008.

(51) Int. Cl.
*A23J 1/00* (2006.01)
*C07K 16/00* (2006.01)

(52) U.S. Cl. ............... 530/412; 530/413; 530/387.1

(58) Field of Classification Search .................... None
See application file for complete search history.

(56) References Cited

U.S. PATENT DOCUMENTS

| 5,151,350 A | 9/1992 | Colbert et al. |
| 2005/0038231 A1 | 2/2005 | Fahrner et al. |

OTHER PUBLICATIONS

Bloom et al., "Detection and reduction of Protein A contamination in immobilized Protein A purified monoclonal antibody preparations", Journal of Immunological Methods, vol. 117, No. 1, Feb. 8, 1989, pp. 83-89.
Carter-Franklin et al., "Fragments of protein A eluted during protein A affinity chromatography", Journal of Chromatography A, vol. 1163, No. 1-2, Sep. 7, 2007, pp. 105-111.
Hahn et al., "Comparison of protein A affinity sorbents III. Life time study", Journal of Chromatography A, vol. 1102, No. 1-2, Jan. 13, 2006, pp. 224-231.
Hermanson et al., "Purification", Chapter 5.1: Immobilized Affinity Ligand Techniques, Academic Press, Inc., San Diego, California, 1992, pp. 317-346.
International Preliminary Report on Patentability received for PCT Patent Application No. PCT/US2009/005142, issued on Mar. 15, 2011, 6 pages.
International Search Report and Written Opinion received for PCT Patent Application No. PCT/US2009/005142, mailed on Jan. 13, 2010, 9 pages.
Nilsson et al., "Chicken Anti-Protein L for the Detection of Small Amounts of Protein L in the Presence of IgG", Hybridoma, vol. 24, No. 2, Apr. 2005, pp. 112-114.

*Primary Examiner* — Maher Haddad
*Assistant Examiner* — James Rogers
(74) *Attorney, Agent, or Firm* — EMD Millipore Corporation

(57) ABSTRACT

The present invention provides methods of quantifying protein leakage from a protein based affinity chromatography media (e.g., protein A, protein G and protein L based affinity chromatography media), where such a protein is used for isolating and/or removing a molecule which binds the protein (e.g., an immunoglobulin).

13 Claims, 3 Drawing Sheets

| Media B | set 1 | set 2 | ave | sd | cv |
|---|---|---|---|---|---|
| Lot 1 | 59.9 | 57.5 | 58.7 | 1.7 | 2.9% |
| Lot 2 | 51.9 | 46.1 | 49.0 | 4.1 | 8.4% |
| Lot 3 | 68.7 | 69.2 | 69.0 | 0.3 | 0.5% |
| Lot 4 | 80.1 | 80.1 | 80.1 | 0.0 | 0.0% |
| Lot 5 | 71.4 | 70.9 | 71.2 | 0.4 | 0.6% |

METHODS FOR QUANTIFYING PROTEIN LEAKAGE FROM PROTEIN BASED AFFINITY CHROMATOGRAPHY RESINS

RELATED APPLICATIONS

This application claims the benefit of priority of U.S. provisional patent application Ser. No. 61/192,082, filing date Sep. 15, 2008, the entire contents of which are incorporated by reference herein in their entirety.

FIELD OF THE INVENTION

The present invention relates to methods for quantifying protein leakage from protein based affinity chromatography resins including, but not limited to, protein A, protein G and protein L based affinity chromatography resins.

BACKGROUND

Protein based affinity chromatography has been widely used in purification of protein, DNA, and other chemical and biological molecules in various scales, ranging from laboratory, pilot to production scales. See, e.g., Hermanson et al., Immobilized Affinity Ligand Techniques, Academic Press, Inc. San Diego, Calif., pgs. 317-346 (1992). Among them, protein A (PrA), protein G (PrG) and protein L (PrL) based affinity chromatography resins are well known and widely used methods for detection and/or purification of immunoglobulins (Ig), however, they each have different specificities with respect to binding Ig.

As an example, PrA based reagents have especially found a widespread use in the field of biotechnology, e.g., in affinity chromatography for capture and purification of antibodies as well as in antibody detection methods. At present, PrA-based affinity media or resins probably are the most widely used affinity media for isolation of monoclonal antibodies and their fragments from different samples including cell culture. Accordingly, various matrices comprising protein A-ligands are commercially available including, for example, ProSep®-vA High Capacity, ProSep® vA Ultra and ProSep® UltraPlus (Millipore) and Protein A Sepharose™, rmp Protein A Sepharose Fast Flow, MabSelect™, MabSelect Xtra™ and MabSelect SuRe® (GE Healthcare), Poros MabCapture A (Applied Biosystems) and Sartobind Protein A (Sartorius).

SUMMARY OF THE INVENTION

Although, protein based affinity chromatography resins, e.g., protein A, G and L based affinity chromatography resins, are highly desirable for the purification of analytes or molecules which bind to them, e.g., immunoglobulins (Ig) in case of PrA, PrG and PrL, one drawback is the leakage of the protein, e.g., protein A, G or L, from the chromatography column along with the analyte or molecule of interest, e.g., an immunoglobulin. For example, protein A based affinity chromatography is highly desirable for large scale purification of antibodies, e.g., because of its ability to specifically bind antibodies at high capacity and for achieving high purity, however, leached PrA, because of its own biological activity and toxicology profile, is usually considered an undesirable impurity in an immunoglobulin eluate. Accordingly, in some aspects of the present invention, it is desirable to monitor PrA leakage and ultimately remove it in subsequent chromatography steps. For example, one way to minimize PrA leakage is to use PrA resins which exhibit the lowest amount of PrA leakage from a chromatography column. Accordingly, in some aspects, the methods of the present invention may be used for identifying protein based affinity chromatography resins including, but not limited to, PrA, PrG and PrL based affinity chromatography resins, which exhibit the lowest amount of leakage from a chromatography column. Such protein based affinity chromatography resins include known resins as well as those which may be developed in the future.

A number of Enzyme-Linked Immunosorbant Assay (ELISA) based screening assays have been developed for detecting PrA leakage from chromatography columns. However, most of these assays are qualitative in nature and generally exhibit a higher variability (e.g., $\geq 25\%$) to be suitable as an analytical tool, for example, for providing a comparison of PrA based affinity chromatography resins, identifying resins that exhibit the lowest amount of PrA leakage and for monitoring leached PrA in antibody elution pools after affinity chromatography and the subsequent chromatography steps.

Fluorescent tags have been used widely in biochemical and chemical research because of high sensitivity and selectivity associated with such tags. For example, leached Protein A from affinity resins has been previously detected using fluorescent dyes, however, such dyes have been used mostly for generating qualitative information, e.g., detection, and do not provide any quantitative information, e.g., the amount of leached PrA. See, e.g., Carter-Franklin, et al, Journal of Chromatography A, 1163: 105-111 (2007).

The present invention is directed, at least in part, to quantitative methods for detecting protein, e.g., PrA, leakage from chromatography media or resins using, e.g., fluorescent tags. Methods according to the invention exhibit a variability of less than 10% and are especially suitable for identifying PrA chromatography resins which exhibit the lowest amount of PrA leakage.

In one aspect according to the present invention, a method for quantifying PrA leakage from a PrA based affinity chromatography resin is provided, where the method comprises the steps of: (a) labeling the PrA based chromatography resin with one or more fluorescent tags; (b) dividing the labeled resin into equal first and second parts; (c) treating first part with suitable means to release the labeled PrA from the resin and adding an excess amount of Ig to the second part; (d) measuring fluorescence ($FL_{digest}$) and PrA concentration ([PrA]) from the treated resin in the first part in step (c); and (e) measuring resin Ig elution concentration ([Ig]) and fluorescence signal in an Ig eluate ($FL_{Ig}$) from the second part in step (c), where PrA leakage is quantified by calculating $\{(FL_{Ig})/((FL_{digest})/[PrA])\}/[Ig]$.

In another aspect according to the present invention, a method for quantifying PrA leakage from a PrA based affinity chromatography resin is provided, where the method comprises the steps of: (a) labeling the PrA based chromatography resin with one or more fluorescent tags; (b) adding an excess amount of Ig to the labeled resin and measuring resin Ig elution concentration ([Ig]) and fluorescence signal in an Ig eluate ($FL_{Ig}$) from the resin; (c) removing residual Ig from the resin followed by treating the resin with suitable means to release the labeled PrA from the resin; and (d) measuring fluorescence ($FL_{digest}$) and PrA concentration ([PrA]) from the treated resin, where PrA leakage is quantified by calculating $\{(FL_{Ig})/((FL_{digest})/[PrA])\}/[Ig]$.

In some embodiments, methods of the invention are used for quantifying the leakage of protein G (PrG) from a PrG based affinity chromatography resin.

Accordingly, in yet another aspect according to the invention, a method for quantifying PrG leakage from a PrG based affinity chromatography resin is provided, which comprises the steps of: (a) labeling the PrG based chromatography resin with one or more fluorescent tags; (b) dividing the labeled resin into equal first and second parts; (c) treating first part with suitable means to release the labeled PrG from the resin and adding an excess amount of Ig to the second part; (d) measuring fluorescence ($FL_{digest}$) and PrG concentration ([PrG]) from the treated resin in the first part in step (c); and (e) measuring resin Ig elution concentration ([Ig]) and fluorescence signal in an Ig eluate ($FL_{Ig}$) from the second part in step (c), where PrG leakage is quantified by calculating $\{(FL_{Ig})/((FL_{digest})/[PrG])\}/[Ig]$.

In yet another aspect, a method for quantifying PrG leakage from a PrG based chromatography resin comprises the steps of: (a) labeling the PrG based chromatography resin with one or more fluorescent tags; (b) adding an excess amount of Ig to the labeled resin and measuring resin Ig elution concentration ([Ig]) and fluorescence signal in an Ig eluate ($FL_{Ig}$) from the resin; (c) removing residual Ig from the resin followed by treating the resin with suitable means to release the labeled PrG from the resin; and (d) measuring fluorescence ($FL_{digest}$) and PrG concentration ([PrG]) from the treated resin, where PrG leakage is quantified by calculating $\{(FL_{Ig})/((FL_{digest})/[PrG])\}/[Ig]$.

In still further embodiments, methods of the invention are used for quantifying the leakage of protein L (PrL) from a PrL based affinity chromatography resin.

Accordingly, in yet another aspect according to the invention, a method for quantifying PrL leakage from a PrL based affinity chromatography resin is provided, which comprises the steps of: (a) labeling the PrL based chromatography resin with one or more fluorescent tags; (b) dividing the labeled resin into equal first and second parts; (c) treating first part with suitable means to release the labeled PrL from the resin and adding an excess amount of Ig to the second part; (d) measuring fluorescence ($FL_{digest}$) and PrL concentration ([PrL]) from the treated resin in the first part in step (c); and (e) measuring resin Ig elution concentration ([Ig]) and fluorescence signal in an Ig eluate ($FL_{Ig}$) from the second part in step (c), where PrL leakage is quantified by calculating $\{(FL_{Ig})/((FL_{digest})/[PrL])\}/[Ig]$.

In another aspect, a method for quantifying PrL leakage from a PrL based chromatography resin comprises the steps of: (a) labeling the PrL based chromatography resin with one or more fluorescent tags; (b) adding an excess amount of Ig to the labeled resin and measuring resin Ig elution concentration ([Ig]) and fluorescence signal in an Ig eluate ($FL_{Ig}$) from the resin; (c) removing residual Ig from the resin followed by treating the resin with suitable means to release the labeled PrL from the resin; and (d) measuring fluorescence ($FL_{digest}$) and PrL concentration ([PrL]) from the treated resin, where PrL leakage is quantified by calculating $\{(FL_{Ig})/((FL_{digest})/[PrL])\}/[Ig]$.

Additionally, without wishing to be bound by theory, it is contemplated that the methods of the invention may be used for quantifying the leakage of any protein and/or fragments thereof, from a protein based affinity chromatography method used for isolating or removing from a mixture, an analyte or molecule that binds the protein.

Accordingly, in yet another aspect according to the present invention, a method for quantifying protein leakage from a protein based affinity chromatography resin is provided, where the method comprises the steps of: (a) labeling the protein based chromatography resin with one or more fluorescent tags; (b) dividing the labeled resin into equal first and second parts; (c) treating first part with suitable means to release the labeled protein from the resin and adding an excess amount of an analyte that binds the protein to the second part; (d) measuring fluorescence ($FL_{digest}$) and protein concentration ([Pr]) from the treated resin in the first part in step (c); and (e) measuring resin analyte elution concentration ([analyte]) and fluorescence signal in an analyte eluate ($FL_{analyte}$) from the second part in step (c), where Pr leakage is quantified by calculating $\{(FL_{analyte})/((FL_{digest})/[Pr])\}/[analyte]$.

In another aspect according to the present invention, a method for quantifying protein leakage from a protein based affinity chromatography resin is provided, where the method comprises the steps of: (a) labeling the protein based chromatography resin with one or more fluorescent tags; (b) adding an excess amount of analyte to the labeled resin and measuring resin analyte elution concentration ([analyte]) and fluorescence signal in an analyte eluate ($FL_{analyte}$) from the resin; (c) removing residual analyte from the resin followed by treating the resin with suitable means to release the labeled protein from the resin; and (d) measuring fluorescence ($FL_{digest}$) and protein concentration ([Pr]) from the treated resin, where Pr leakage is quantified by calculating $\{(FL_{analyte})/((FL_{digest})/[Pr])\}/[analyte]$.

In various embodiments, methods of the invention may further include the step of removing the leached protein, e.g., PrA, PrG or PrL, using one or more of cation exchange chromatography, anion exchange chromatography and hydrophobic exchange chromatography, weak partitioning chromatography, hydroxyapatite chromatography, or any combinations thereof. Exemplary chromatography formats include, but are not limited to, packed column and a membrane device format.

In various embodiments of the methods of the invention, a fluorescent tag is selected from the group consisting of Alexa Fluor 488™ (Invitrogen, Carlsbad, Calif.), Dylight 488™ (ThermoFisher, Waltham, Mass.), HiLyte Fluor™ 488, 5-FAM™, SE and 6-FAM™, SE (Anaspec, San Jose, Calif.).

In various embodiments, suitable means for releasing the labeled protein from the resin, e.g., PrA, PrG and PrL, used in the methods of the invention include chemical treatment or enzymatic treatment. Exemplary enzymatic treatments include the use of an enzyme that digests the protein, e.g., PrA, PrG or PrL, including, but not limited to, for example, trypsin, pepsin, chymotrypsin, thermolysin and subtlelysin. Exemplary chemical treatments include the use of a suitable acid or base.

In various embodiments of the methods of the invention, commercially available PrA based affinity chromatography resins are compared using the methods of the invention, in order to identify those which exhibit the lowest amount of PrA leakage. Exemplary resins include, but are not limited to, ProSep®-vA High Capacity, ProSep® vA Ultra and ProSep® UltraPlus (Millipore); Protein A Sepharose™, MabSelect™, MabSelect Xtra™ and MabSelect SuRe® (GE Healthcare); Sartobind Protein A (Sartorius); and POROS® MabCapture™ A (Applied Biosystems).

In some aspects of the methods of the invention, residual Ig (e.g., IgG) may be removed from the resin using well known techniques in the art including, e.g., use of 6M guanidinium HCL or 4-8M urea.

In some aspects of the methods of the invention, an excess amount of an analyte or molecule (e.g., Ig) is an amount at least 2-5 times greater than the maximum binding capacity of the protein based affinity chromatography resin or media used for isolating or removing the analyte or molecule. In some embodiments, the analyte or molecule is an Ig (e.g., IgG) which binds a PrA based affinity chromatography media or resin, where an excess amount of the Ig (e.g., IgG) is at least 2, or at least 3, or at least 4, or at least 5, or greater than 5 times the binding capacity of the resin. In general, the excess amount of the analyte or molecule (e.g., Ig) can be determined based on the maximum binding capacity of the resin typically provided by the manufacturer of the resin or may be readily calculated by one of ordinary skill in the art based on well known techniques in the art.

Fluorescence can be measured using any suitable means including, but not limited to, the use of a fluorometer. The sample loading for detection using a fluorometer could be in a cuvette or a well-pate format.

In various embodiments of the methods of the invention, the Ig (e.g., IgG) can be eluted using any suitable means such as, for example, the use of a suitable pH. In an exemplary embodiment, a suitable pH used for IgG elution is a pH from about 2.0 to about 4.0. In a particular embodiment, Glycine at pH 2.0 is used for IgG elution.

BRIEF DESCRIPTION OF THE DRAWINGS

FIG. 3 depicts a Table summarizing PrA leakage values of five different lots of a silica based protein affinity resin, each tested with two different batches of Alexa Fluor 488. As depicted in the Table, variability of less than 8.4% is achieved for the two sets of experiments using two different batches of the fluorescent dye.

DETAILED DESCRIPTION OF THE INVENTION

Figure 1:
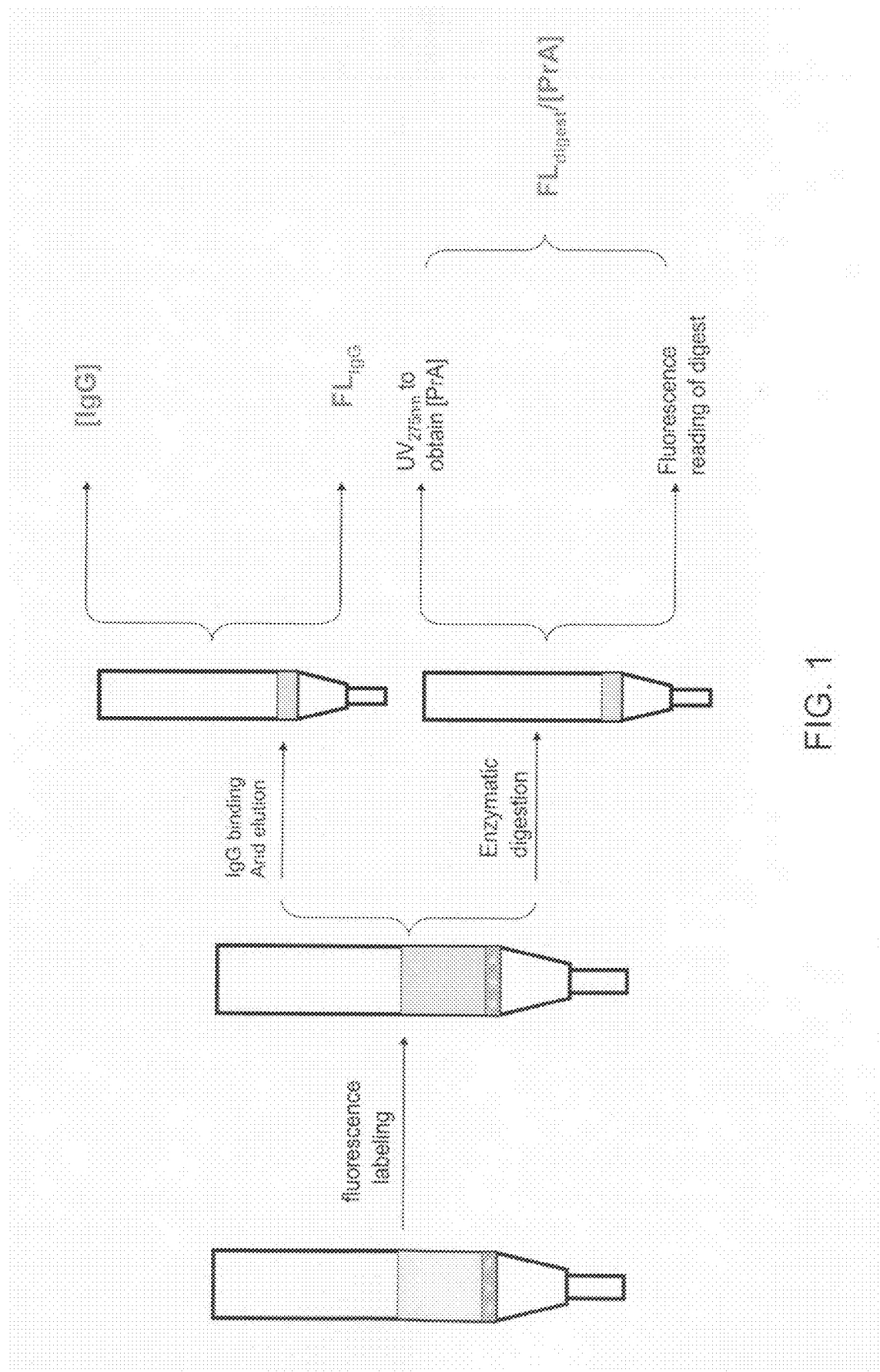
FIG. 1 depicts a schematic of an exemplary method according to the invention, in which PrA is labeled with fluorescent dye (Alexa Fluor™ 488). Briefly, as depicted in FIG. 1, the labeled media is split into two 1 ml fractions. One fraction is treated enzymatically with trypsin. The ratio $FL_{digest}/[PrA]$ is obtained by reading the supernatant at $UV_{275}$ nm on a UV/Vis spectrophotometer and at emission 519 nm on a fluorometer with excitation at 495 nm. The other fraction is exposed to Ig (e.g., IgG) with an approximate 5 times of estimated capacity of media, which constitutes an excess amount of IgG. Once excess IgG is washed off with PBS (10 mM phosphate saline buffer), the IgG bound to PrA media is eluted with 0.1 M glycine pH 2. After gentle mixing, the IgG elution is analyzed on a UV/Vis spectrophotometer at $UV_{280}$ nm ([IgG]) and emission 519 nm on a fluorometer with excitation at 495 nm ($FL_{IgG}$).

The present invention relates to methods of quantifying protein, e.g., PrA, PrG or PrL, leakage from protein based affinity chromatography media or resin, e.g., PrA, PrG and PrL based affinity chromatography media or resin. Without wishing to be bound by theory, it is contemplated that the methods according to the invention can be used for quantifying the leakage of any protein from a protein based chromatography media or resin, where the protein is used for isolating or removing a molecule that binds the protein, including but not limited to, e.g., protein A, protein G and protein L which bind Ig.

In order that the present disclosure may be more readily understood, certain terms are first defined. Additional definitions are set forth throughout the detailed description.

I. DEFINITIONS

As used herein, the term "protein A" or "PrA" encompasses protein A recovered from a native source, e.g., from the bacterium *Staphylococcus aureus*, protein A produced synthetically (e.g., by peptide synthesis or by recombinant techniques), including variants or derivatives thereof which retain the ability to bind proteins which have a $C_{H2}/C_{H3}$ region such as, for example, immunoglobulins. Commercial sources of PrA include Repligen, GE Healthcare, Fersenius Medical, and Fermatech.

The term "chromatography," as used herein, refers to any kind of purification technique which separates the analyte (e.g., an immunoglobulin or Ig) of interest from other molecules in the mixture, for example, by their differences in partition between a solid substrate and the mobile phase, including but not limited to, solution, buffer or solvent and allows the analyte of interested to be isolated.

As used herein, the term "affinity chromatography," "affinity separation," or "affinity purification," as used herein, refers to any purification or assaying technique which involves the addition of a sample containing a target analyte or molecule (e.g., an immunoglobulin or Ig) to a solid support which carries on it a protein which binds the analyte, e.g., PrA, PrG and PrL. Subsequent to the binding of a target analyte or molecule (e.g., an Ig) to the protein (e.g., PrA) and the flowthrough of the undesired impurities, the target analyte or molecule may be eluted using suitable means. For example, the analyte, such as an IgG, may be recovered using a suitable elution buffer having a suitable pH, e.g., a pH in the range from about 2 to about 5, or in the range from about 2 to about 4. Examples of elution buffers for this purpose include citrate, glycine, or acetate buffers.

The term "PrA based affinity chromatography" or "Protein A based affinity chromatography," as used herein, refers to the separation or purification of substances and/or molecules, such as immunoglobulins, using protein A or a derivative or variant thereof, where the PrA is generally immobilized on a solid support.

The term "PrG based affinity chromatography" or "Protein G based affinity chromatography," as used herein, refers to the separation or purification of substances and/or molecules, such as immunoglobulins, using protein G or a derivative or variant thereof, where the PrG is generally immobilized on a solid support.

The term "PrL based affinity chromatography" or "Protein L based affinity chromatography," as used herein, refers to the separation or purification of substances and/or molecules, such as immunoglobulins, using protein L or a derivative or variant thereof, where the PrL is generally immobilized on a solid support.

The term "solid phase" or "solid support" generally refers to a non-aqueous matrix to which the protein used for isolating or removing an analyte or molecule of interest, e.g., protein A (PrA), protein G (PrG) or protein L (PrL) can adhere or be covalently bound. For example, PrA may be coupled to variety of materials such as, for example, agaroses, polysaccharides, dextrans, silica gels, synthetic polymers (polystrene-divinylbenzene, polyacrylate, polymethacrylate, polyacrylamide, polyvinyl alcohol, polysulfone, polycarbonate, polyvinyl ether and their corresponding copolymers) and glass beads. The solid support format includes, but is not limited to, a purification column, discontinuous phase of discrete particles, packed bed column, and expanded bed column, membrane, etc. In some embodiments, as an optional preliminary step, the solid phase for the protein A affinity chromatography may be equilibrated with a suitable buffer before chromatography of the protein of interest. An exemplary equilibration buffer contains 10 mM phosphate saline buffer pH 7.4.

The term "affinity resin" or "affinity chromatography resin," as used herein, refers to a chromatographic support to which a chromatography ligand (e.g., PrA or PrG or PrL) is attached. The ligand is capable of binding to a molecule of interest (e.g., an immunoglobulin) which is to be purified or removed from a mixture. Exemplary protein A based affinity chromatography resins for use in protein A based affinity chromatography include protein A immobilized onto a controlled pore glass backbone, e.g., the PROSEP A™ and PROSEP vA™ resins, High Capacity, Ultra and PROSEP Ultra Plus (Millipore Inc.); protein A immobilized on a polystyrene solid phase, e.g. the POROS 50A™ resin and POROS MabCapture A™ (Applied BioSystems Inc.); or protein A immobilized on an agarose solid phase, for instance the rPROTEIN A SEPHAROSE FAST FLOW™ or MABSELECT™ resin (GE Healthcare).

The eluted Ig (e.g., IgG) may be subjected to additional purification steps either prior to, or after, the protein A affinity chromatography step. Exemplary further purification steps include, but are not limited to, filtration, hydroxyapatite chromatography, hydrophobic interaction chromatography (HIC), ammonium sulphate precipitation, anion or cation exchange chromatography, ethanol precipitation, reverse phase HPLC, weak partitioning chromatography, chromatofocusing, gel filtration, etc.

In some embodiments, the eluted Ig (e.g., IgG) may be formulated in a pharmaceutically acceptable carrier and is used for various diagnostic, therapeutic or other uses known for such molecules.

As used herein, the terms "protein leaching," "protein leakage," "leached protein," "Pr leaching," "Pr leakage" and "leached Pr," refer to the detachment or washing of protein (Pr) (including intact and/or fragments thereof) from a solid phase to which it is bound. In some embodiments, leakage of PrA, PrG or PrL is quantified from PrA, PrG or PrL based affinity chromatography resins using the methods of the invention. Protein leakage may result due to many different reasons. For examples, PrA leakage or PrA leaching may result due to reasons such as mechanical shearing, low/high pH exposure, contact to immunoglobulin, proteolytic activity etc. Protein A leaching can be qualitatively measured using various techniques that are well known in the art, including, enzyme linked immunosorbent assay (ELISA), SDS PAGE, Western blot, high pressure liquid chromatography (HPLC), mass spectrometry, etc. The amount of leached PrA is generally represented as ng PrA/ml affinity matrix, or it may be represented as ng protein A/mg antibody.

As used herein, the term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

In some embodiments, an immunoglobulin is an IgG antibody. Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fc and/or Fv fragments.

The term "antigen-binding fragment" refers to a polypeptide portion of an immunoglobulin or antibody that binds an antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', $F(ab')_2$, Fv, single chains, and single-chain antibodies.

II. wtPrA STRUCTURE AND IMMUNOGLOBULIN BINDING SITES

PrA is about a 42-kDa protein derived from the bacterium *Staphylococcus aureus* and contains five tandem highly homologous extracellular immunoglobulin (Ig)-binding domains at the N-terminus, designated E, D, A, B and C. Each extracellular domain of PrA possesses distinct Ig-binding sites. One site is for Fcγ (the constant region of IgG class of Ig) and the other is for the Fab portion of certain Ig molecules (the portion of the Ig that is responsible for antigen recognition). It has been reported that each of the domains contains a Fab binding site. The non-Ig binding portion of SpA is located at the C-terminus and is designated the X region or X-domain.

The cloning of the gene encoding wtPrA is described in U.S. Pat. No. 5,151,350, the entire contents of which are incorporated by reference herein in their entirety.

III. EXEMPLARY Pr BASED AFFINITY CHROMATOGRAPHY MEDIA

Methods of the invention can be used for quantifying leakage of a protein from protein affinity chromatography media or resin, where such protein based affinity chromatography resin is used for isolating or purifying a molecule which binds the protein. In exemplary embodiments, methods of the invention are used for quantifying the leakage of a protein from an affinity chromatography media or resin, where such media or resin is used for isolating or removing from an immunoglobulin from a mixture, including but not limited to, PrA, PrG and PrL and derivatives, variants and fragments thereof.

Exemplary protein A based resins which may be used in the methods of the invention include, but are not limited, to PROSEP vA High Capacity, PROSEP A Ultra, PROSEP Ultra Plus (Millipore), Protein A Sepharose FastFlow, rmp Protein A Sepharose FastFlow, MabSelect, MabSelect Xtra, MabSelect SuRe (GE Healthcare), POROS A, POROS MabCapture A (Applied Biosystems), and Sartobind Protein A (Sartorius). Exemplary protein G based resins include, but are not limited, to PROSEP-G (Millipore), Protein G Sepharose™ 4 Fast Flow (GE Healthcare), POROS G (Applied Biosystems).

IV. EXEMPLARY FLUORESCENT TAGS AND MEASUREMENT OF FLUORESCENCE

Any suitable fluorescent tag or dye which is capable of labeling a protein may be used in the methods of the invention. In general, it is desirable to use a fluorescent tag or dye which has an extinction coefficient $\epsilon_{max}$ no less than 70,000 cm$^{-1}$M$^{-1}$ with a quantum yield of >80% and exhibits minimal photo bleaching or quenching. The dye used should be stable under the conditions of the experiment, e.g., a pH range of about 1.0 to about 10.0. For protein based affinity chromatography media, it is desirable to use amine, thiol and carboxy reactive dyes. Exemplary amine reactive fluorescent dyes include, but are not limited to, succinimidyl esters including sulfosuccinimidyl esters, isothiocyanates, sulfonyl chlorides, and tetrafluorophenyl esters. Exemplary thiol reactive dyes include, but are not limited to, maleimides, phenylmercury, iodoacetamide, thiosulfates, rhodamine derivative, and benzoxadiazo derivatives. In exemplary embodiments, dyes which may be used for labeling a protein based affinity chromatography media include AlexaFluor 488 (Invitrogen, Carlsbad, Calif.), Dylight 488 (ThermoFisher, Waltham, Mass.), HiLyte Fluor™ 488, and 5-FAM, SE and 6-FAM, SE (Anaspec, San Jose, Calif.).

Methods of the present invention are generally based on the measurement of fluorescence. In general, fluorescence is a type of optical spectroscopy in which a molecule is promoted to an electronically excited state by absorption of ultraviolet, visible, or near infrared radiation. The excited molecule then decays back to the ground state or to a lower-lying excited electronic state by emission of light, which is detected using an instrument such as a fluorometer. In case of the methods of the present invention, the fluorescent dye is a reactive dye which binds to a protein, e.g., PrA. It is desirable that such a dye maintains the fluorescent intensity within about 20% of the maximum intensity under the experimental conditions used in the methods of the invention, e.g., use of a pH in the range of about 1.0 to about 10.0 for at least half an hour.

V. METHODS OF RELEASING THE LABELED PROTEIN FROM THE PROTEIN BASED AFFINITY CHROMATOGRAPHY RESIN

Following the labeling of a protein in a protein based chromatography media or resin, the covalently bound protein is released from the affinity media or resin. Methods for releasing covalently bound labeled protein from the affinity media include, but are not limited to, chemical and enzymatic methods. In exemplary chemical treatment methods, acid or base catalyzed hydrolysis may be used which does not interfere with the UV absorption significantly. Exemplary acids which may be used in the methods of the invention include, but are not limited to, monovalent acids such as, e.g., hydrochloric acid, divalent acids, such as, sulfuric acid, and trivalent acids, such as phosphoric acid. Exemplary bases which may be used in the methods of the invention include, but are not limited to, sodium hydroxide, potassium hydroxide, and cesium hydroxide. Additionally, chemicals such as CNBr may be used which can break certain peptide bounds, thereby to release the labeled protein from the solid support to which it is attached. See, e.g., Uhlen and Nilsson, In Proc. Biotech 85 (Europe), pg. 173 (1985).

Exemplary enzymatic treatment methods include, but are not limited to, the use of an enzyme capable of digesting a protein. Exemplary enzymes include, but are not limited to, e.g., trypsin, pepsin, chymotrypsin, thermolysin and subtlelysin.

VI. MEASURING FLUORESCENCE AND PROTEIN CONCENTRATION FROM THE CHEMICALLY OR ENZYMATICALLY TREATED RESIN

Chemically or enzymatically treated resin is subsequently filtered to obtain the particulate free supernatant. The supernatant contains the digested labeled protein (e.g., PrA), the fluorescence of which can be measured, for example, using a UV/Vis spectrophotometer at 275 nm. This reading includes the UV adsorption contributed by the digested protein (e.g., protein A and protein A fragments digested from resin). In order to specifically obtain concentration of the protein (e.g., PrA concentration or [PrA]), the contribution from the chemical or enzyme and fluorescent dye in the fluorescence reading need to be subtracted. The contribution from chemical or enzyme, $UV_{enz/chem}$, used to release the protein (e.g., PrA) can be detected by measuring the starting chemical or enzyme concentration factoring in the dilution factor. Also, the contribution from the fluorescent tag or dye can be calculated by obtaining the UV absorption at peak of the fluorescent tag or dye, which is usually UV at excitation wavelength, $UV_{max}$. The ratio $UV_{275}/UV_{max}$ (f) for each dye can be typically obtained from the vendor. As an example, assuming that the extinction coefficient for Protein A is 0.149, protein A concentration can be obtained using the formula: $[UV_{275} - UV_{enz/chem} - UV_{max} \times f]/0.149$.

Fluorescence is generated by excitation of a molecule at a certain wavelength and detection at longer wavelength to receive the emission spectra. In general, the optimum excitation and emission wavelengths recommended by the fluorescent dye vendor may be used. For example, for the dye Alexa Fluor 488 from Invitrogen, excitation wavelength is 495 nm and emission wavelength is 519 nm. Also, fluorescence reading can be obtained from supernatant with serial dilution if necessary. Fluorescence is typically read in a cuvette or a well plate format fluorometer at a set temperature, such as 25° C.

VII. MEASURING ELUATE CONCENTRATION

In the various methods according to the claimed invention, concentration of the eluted molecule or analyte of interest (e.g., immunoglobulin or Ig) is needed for the calculation of leached protein, which is measured as ng of leached protein per mg of eluted molecule. In exemplary methods according to the invention, the eluted molecule is an immunoglobulin, which is isolated using PrA, PrG or PrL based affinity chromatography media. In some embodiments, the eluted molecule, e.g., an immunoglobulin, is released from the affinity chromatography media using changes in the pH, ionic strength/salt concentration, and/or temperature via gradient or step changes. For example, in case of IgG, elution from a PrA based chromatography media is typically achieved by lowering the elution pH to less than 5, but no lower than pH 2, and most desirably between pH 2 and 4. Exemplary elution buffers include acetic acid, glycine, and citric acid. In some embodiments, elution of IgG is achieved via flow of elution buffer at a rate of 2000 cm/hr or less, 1000 cm/hr or less, 800 cm/hr or less, 600 cm/hr or less, 200 cm/hr or less, 100 cm/hr or less, or 50 cm/hr or less. In general, the slower the flow rate, the more IgG binds to the media and the elution IgG concentration is typically higher. When the elution flow rate is <5 cm/hr, the media binds close to the maximum amount of IgG it can bind, and thus reaches the static binding capacity. Excess amount of IgG is used for static binding capacity test, usually >3-5 times the media maximum binding capacity. Accordingly, the amount of leached protein A is usually defined as ng of Protein A per mg of IgG in solution.

This invention is further illustrated by the following examples which should not be construed as limiting. The contents of all references, patents and published patent applications cited throughout this application, as well as the Figures, are incorporated herein by reference.

EXAMPLES

Example 1

Labeling of PrA Based Affinity Chromatography Resins With a Fluorescent Tag

Controlled pore glass based protein A affinity chromatography resins (e.g., ProSep®-vA High Capacity and ProSep® Ultra PrA (Millipore)) were labeled with the Alexa Fluor 488 dye. Briefly, 1 mg of the Alexa Fluor 488 dye (Invitrogen, Carlsbad, Calif.) was dissolved in about 1 ml of DMSO. Approximately 3 mls of each of the PrA resin was treated with $NaHCO_3$ (0.1 M pH 8.4), vacuum dried and packed into 15 mls Evergreen columns (Evergreen Scientific, Los Angeles, Calif.). Approximately 3 mls of $NaHCO_3$ was added to each column and the columns are capped and wrapped in aluminum foil. About 100 µl of the dye was added to each column and put on a shaker for about 0.5 hours. Another 100 µl dye solution was added to the column and shaken for another hour. The column was subsequently slurried and washed three times with about 2 column volumes of $NaHCO_3$ each time, three times with about 2 column volumes of 20% ethanol each time and twice with about 2 column volumes of $NaHCO_3$ each time.

The labeled resins were subsequently divided into parts of 1 ml and transferred into vials.

Example 2

Enzymatic Treatment of the Fluorescent Tag Labeled PrA Resins

One fraction of the fluorescently labeled PrA resins was subsequently enzymatically digested. PrA resin with no fluorescent label was used as a control. Briefly, 1 ml of each of the PrA resin was treated with 0.1 M $NH_4HCO_3$ and vacuum dried. Trypsin was dissolved in 0.1 M $NH_4HCO_3$ and the UV measurement at 275 nm was taken such that it was between 0.7 and 1. About 3 ml of the trypsin solution was subsequently added to each of the resins and incubated at 37° C. for about 2 hours. The incubated media slurry was filtered through a 7 mL Evergreen drippy column to remove the supernatant from the media. Filtrate measurement was taken at $UV_{275\ nmD}$ and $UV_{275\ nmT}$ of Trypsin was subtracted from this value. Also, a $UV_{495\ nmF}$ measurement of the filtrate was taken. An extinction coefficient of 0.149 was used to obtain Protein A concentration using the formula ($UV_{275\ nmD}$×dilution factor−$UV_{275\ nmT}$−f×$UV_{495\ nmF}$×dilution factor)/0.149, which gave the concentration of digested Protein A, [PA]. The value of f is the ratio of UV extinction coefficient of the dye at $UV_{275\ nm}$/$UV_{495\ nm}$ and is provided by the vendor of fluorescent dye.

The fluorescence of the above filtrate was measured at a ~2000× dilution (with 0.1 M Glycine), which gave the value $[FL_{digest}]$.

Example 3

Measuring IgG Eluate Concentration/Static Capacities of the Labeled and Unlabeled Resins IgG eluate concentration/static capacities of labeled and unlabeled protein A based affinity chromatography resins were determined as follows. Measurement of static capacity is also an indication of whether or not labeling of a PrA resin with a fluorescent tag disrupts the interaction of the PrA resin with IgG, for example.

Figure 2:
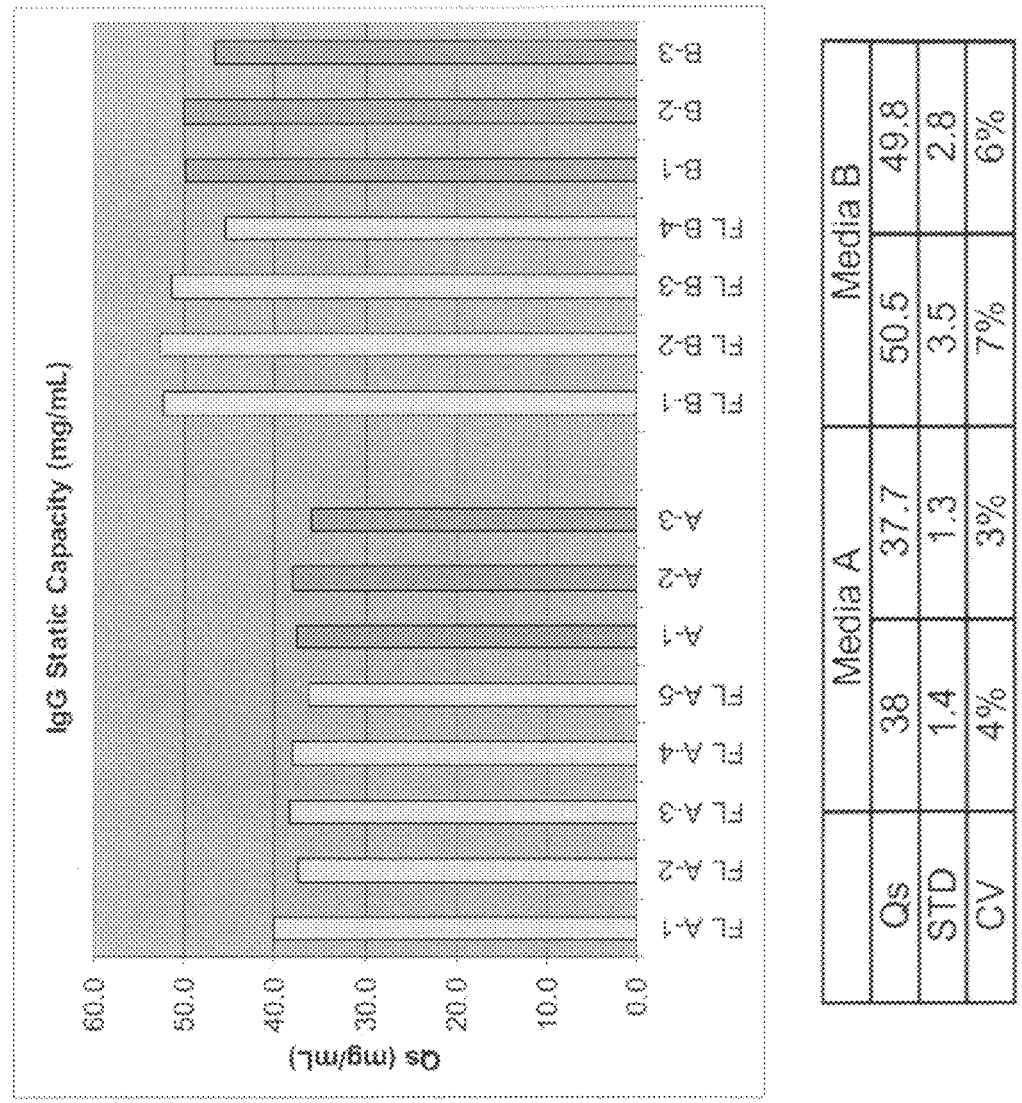
FIG. 2 depicts a graph demonstrating that the static IgG binding of labeled (e.g., with Alexa Fluor 488) and unlabeled PrA is equivalent. Briefly, fluorescently labeled type A resin (FL-A-1 through FL-A-5) and unlabeled resin (A-1 through A-3) from the same batch were tested for their IgG static binding capacity on three different days. The results, as depicted in the graph in FIG. 2, demonstrate that labeled and unlabeled type A PrA based affinity chromatography resins have equivalent static binding capacity values. The same experiment was conducted with a different PrA based affinity chromatography type B resin, represented by FL-B-1 through FL-B-4 for the labeled resin and B1 through B3 for the unlabeled resin. Again, as demonstrated by the graph in FIG. 2, both the labeled and unlabeled type B resins exhibit equivalent IgG static binding capacity values. Accordingly, fluorescence labeling presents minimal interference on PrA-IgG affinity interaction for different resins. The results are also summarized in the Table in FIG. 2. The static binding capacity of resins (Qs) from labeled and unlabeled type A resin (Media A) are shown on the left side of the Table and the same from labeled and unlabeled type B resin (Media B) are shown on the right side of the Table. Standard Deviation (STD) and coefficient of variance (CV) are presented as well. Test variability for labeled and unlabeled Media A (4% vs 3%) as well as for Media B (7% vs 6%) are comparable.

Labeled and unlabeled PrA resins were each measured in 1 ml volumes (Evergreen Scientific, Los Angeles, Calif.) with tapping. Each sample was reslurried and equilibrated with 10 ml of 10 mM phosphate saline buffer (PBS). Elution by gravity of PBS was discarded, followed by the addition of 5 ml of 0.1 M pH 2 glycine. Elution was discarded. Another 5 ml of 0.1 M pH 2 glycine was added and the elution was collected as $Fr_{bkgd}$. Two 5 ml portions of PBS were added to equilibrate the media before the addition of 5 ml of ~50 mg/mL polyclonal hIgG (Sigma-Aldrich, Milwaukee, Wis.). This was followed by another two 5 ml portions of PBS. All PBS and IgG elutions by gravity were discarded. Glycine (5 ml, 0.1 M, pH 2) was added and the eluate was collected, labeled as $FR_1$. Another 5 ml of glycine solution was added and the eluate was collected, labeled as $FR_2$. A UV measurement at 280 nm was taken for obtaining elution IgG concentration [IgG]. The results of one such experiment measuring the static capacities of the PrA resins is depicted in FIG. 2. As demonstrated by FIG. 2, interaction of each of the PrA resins with IgG was not disrupted by the addition of the fluorescent dye to the resin. Also, measurements of static capacities are depicted in the Table in FIG. 2.

The eluate concentration [IgG] is measured at $A_{280\,nm}$ using $FR_1 \times$dilution factor+$A_{280\,nm}$ of $FR_2 \times$dilution factor)/extinction coefficient of IgG. Fluorescence is subsequently measured at 519 nm with excitation at 495 nm using a Jasco FP-6500 fluorometer (Great Dunmow, UK). The fluorescence value of $FR_1$ and $FR_2$ of unlabeled media is subtracted from that of the corresponding labeled media. The sum of the fluorescence signal of fraction 1 and fraction 2 from the above is further subtracted by $Fr_{bkgd}$ to obtain $[FL_{IgG}]$. Protein A leached from the resin is calculated using the following formula: $\{(FL_{IgG}/((FL_{digest})/[PrA]))/[IgG]$.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method for quantifying PrA leakage from a PrA based affinity chromatography resin, the method comprising the steps of:
   (a) labeling the PrA in the PrA based chromatography resin with one or more fluorescent tags;
   (b) dividing the labeled resin into equal first and second parts;
   (c) treating first part with suitable means to release the labeled PrA from the resin and adding an excess amount of immunoglobulin (Ig) to the second part;
   (d) measuring fluorescence ($FL_{digest}$) and PrA concentration ([PrA]) from the treated resin in the first part in step (c); and
   (e) measuring resin Ig eluate concentration ([Ig]) and fluorescence signal in an Ig eluate ($FL_{Ig}$) from the second part in step (c),
   wherein PrA leakage is quantified by calculating $\{(FL_{Ig}/((FL_{digest})/[PrA]))\}[Ig]$.

2. The method of claim 1, wherein the immunoglobulin is an IgG.

3. The method of claim 1, further comprising the step of removing the leached PrA using one or more of cation exchange chromatography, anion exchange chromatography and hydrophobic exchange chromatography, weak partitioning chromatography, hydroxyapatite chromatography, or any combinations thereof.

4. The method of claim 1, wherein the fluorescent tag is an amine reactive dye.

5. The method of claim 1, wherein the suitable means comprises chemical treatment.

6. The method of claim 1, wherein the suitable means comprises enzymatic treatment.

7. The method of claim 6, wherein the enzymatic treatment comprises the use of trypsin, pepsin, chymotrypsin, thermolysin and subtlelysin.

8. The method of claim 5, wherein the chemical treatment comprises use of an acid or base.

9. The method of claim 1, wherein the fluorescence is measured using a fluorometer.

10. The method of claim 1, wherein the Ig is eluted using a suitable pH.

11. The method of claim 1, wherein the Ig is monoclonal.

12. The method of claim 1, wherein the Ig is polyclonal.

13. The method of claim 1, wherein the immunoglobulin is an IgG.

* * * * *